United States Patent
Perry et al.

(12) 
(10) Patent No.: US 6,236,709 B1
(45) Date of Patent: May 22, 2001

(54) CONTINUOUS HIGH SPEED TOMOGRAPHIC IMAGING SYSTEM AND METHOD

(75) Inventors: John L. Perry, Herndon; Thomas D. Gamble, Annandale, both of VA (US)

(73) Assignee: Ensco, Inc., Springfield, VA (US)

( * ) Notice: Subject to any disclaimer, the term of this patent is extended or adjusted under 35 U.S.C. 154(b) by 0 days.

(21) Appl. No.: 09/304,670

(22) Filed: May 4, 1999

Related U.S. Application Data (60) Provisional application No. 60/084,073, filed on May 4, 1998.

(51) Int. Cl.⁷ .................................................. G01N 23/04
(52) U.S. Cl. .................................. 378/57; 378/9; 378/25; 378/56
(58) Field of Search ................................. 378/9, 25, 56, 378/57, 114

(56) References Cited

U.S. PATENT DOCUMENTS

| | | |
|---|---|---|
| 4,145,614 | 3/1979 | Kowalski . |
| 4,991,190 | 2/1991 | Mori . |
| 5,068,882 * | 11/1991 | Eberhard .................................. 378/4 |
| 5,253,171 | 10/1993 | Hsiao et al. . |
| 5,335,255 * | 8/1994 | Seppi et al. .............................. 378/4 |
| 5,367,552 | 11/1994 | Peschmann . |
| 5,442,672 | 8/1995 | Bjorkholm et al. . |
| 5,483,569 | 1/1996 | Annis . |
| 5,493,517 | 2/1996 | Frazier . |
| 5,524,133 | 6/1996 | Neale et al. . |
| 5,583,904 | 12/1996 | Adams . |
| 5,629,966 | 5/1997 | Dykster et al. . |
| 5,886,353 * | 3/1999 | Spivey et al. . |
| 5,991,358 * | 11/1999 | Dolazza et al. . |
| 6,018,562 * | 1/2000 | Willson ................................ 378/9 |
| 6,052,433 * | 4/2000 | Chao . |

\* cited by examiner

Primary Examiner—David V. Bruce
Assistant Examiner—Pamela R. Hobden
(74) Attorney, Agent, or Firm—Nixon Peabody LLP; Daniel W. Sixbey

(57) ABSTRACT

The continuous, high speed, tomographic imaging system moves a closed package containing concealed objects continuously along a conveyor belt past three spaced sensing stations. At each sensing station a plurality of X-ray sources each emit a fan beam in the same scan plane which passes through the package to a plurality of detectors opposite to the X-ray sources. One scan is a vertical perpendicular scan plane relative to the direction of travel of the package along the conveyor belt and the remaining two scan planes are horizontal scan planes at right angles and transverse to the direction of travel. One horizontal scan plane is a left to right scan plane while the remaining scan plane is a right to left scan plane. Each detector provides multiple energy outputs (5) for the same data point in a scan slice, and the detector outputs are stored until all three sensing stations have scanned the same cross sectional view of the package in three directions. Scans are sequentially taken as the package moves continuously through the sensing stations and scanned data corresponding to cross sectional views of the package is accumulated. The stored data is calibrated and normalized and then used in a CT algebraic reconstruction technique. This is a multispectral CT reconstruction, where the density of a reconstructed object is determined by the attenuation which it causes in the scanning X-rays while the atomic number of the object is determined from the multiple energy scan output. In a classifier, the density and atomic number are compared to a stored look up table containing density and atomic number identification values for specific objects to be located.

18 Claims, 5 Drawing Sheets

CROSS SECTION OF THE BASIS FUNCTION. DIAMETER = 3.71 PIXEL INTERVALS

FIG. 9

PLANE VIEW OF BASIS FUNCTION POSITION AND OVERLAP

FIG. 10

COMPUTATION OF WEIGHT OF A BASIS FUNCTION CENTERED AT (u,v) FOR A
PROJECTION ALONG A RAY DEFINED FROM A SOURCE AT (x,y) TO A DETECTOR AT (d,e).

CONTINUOUS HIGH SPEED TOMOGRAPHIC IMAGING SYSTEM AND METHOD

This application is a continuation-in-part application of provisional application Ser. No. 60/084,073 filed May 4, 1998.

BRIEF DESCRIPTION OF THE INVENTION

The present invention relates generally to the X-ray computed tomographic imaging of articles, and more particularly to a continuous high speed tomographic imaging system with a three plane source detector assembly and method for reconstruction imaging.

BACKGROUND OF THE INVENTION

X-ray Computed Tomography (CT) is in wide use at the present time in the medical field for medical imaging. The use of CT produces a cross sectional image from a plurality of attenuation measurements taken at a plurality of angles around the object. However, none of the medical derived CT systems have been designed to meet the real-time inspection requirements for industrial applications. Such systems require an extensive time frame to accomplish scanning, acquire data and provide an image therefrom.

Attempts have been made to provide improved CT systems for nonmedical use. One such system employs an X-ray unit to pre-scan an object, and the pre-scan data is used to select locations for subsequent CT scanning. This system, which is illustrated by U.S. Pat. No. 5,367,552 to Peschmann, uses a rotating CT scanning unit which requires an object to remain stationary during scanning.

In an attempt to improve tomographic reconstruction imaging, algebraic reconstruction techniques (ART) have been employed, but known ART systems have many shortcomings in providing high quality reconstructed imagery. U.S. Pat. No. 5,442,672 to Bjorkholm et al. discloses a three-dimensioned reconstruction based upon a limited number of X-ray projections where algebraic reconstruction techniques are used to reconstruct an image from projected images.

SUMMARY OF THE INVENTION

It is a primary object of the present invention to provide a novel and improved continuous, high speed, tomographic imaging system and method to provide real time inspection of objects to identify an object concealed in a container.

Another object of the present invention is to provide a novel and improved continuous, high speed, tomographic imaging system and method utilizing a three plane source-detector geometry to provide an enhanced tomographic imaging reconstruction.

Yet another object of the present invention is to provide a novel and improved continuous, high speed, tomographic imaging system and method using a multiple plane scanning geometry and a basis function algebraic reconstruction technique whereby attenuation in an image area is modeled as the sum of smooth functions with diameters of at least two pixel intervals. The value appropriate for a pixel is determined by the sum of the basis functions times their amplitudes at the pixel position.

A further object of the present invention is to provide a novel and improved continuous, high speed, tomographic imaging system employing a three plane source-detector geometry which includes a vertical ray path in one plane and two horizontal ray paths in two other planes. The horizontal ray paths are displaced along the line of travel of an object begin scanned.

A still further object of the present invention is to provide a novel and improved continuous, high speed, tomographic imaging system using three stationary X-ray source arrays and three stationary detector arrays to scan objects continuously moving past the arrays.

These and other objects of the present invention are achieved by providing a continuous, high speed, tomographic imaging system wherein a closed package containing concealed objects is moved continuously along a conveyor belt past three spaced sensing stations. At each sensing station a plurality of X-ray sources each emit a fan beam in the same scan plane which passes through the package to a plurality of detectors opposite to the X-ray sources. One scan plane is a vertical perpendicular scan plane relative to the direction of travel of the package along the conveyor belt and the remaining two scan planes are horizontal scan planes at right angles and transverse to the direction of travel. One horizontal scan plane is a left to right scan plane while the remaining scan plane is a right to left scan plane. Each detector provides multiple energy outputs (5) for the same data point in a scan slice, and the detector outputs are stored until all three sensing stations have scanned the same cross sectional view of the package in three directions. Scans are sequentially taken as the package moves continuously through the sensing stations and scanned data corresponding to cross sectional views of the package is accumulated. The stored data is calibrated and normalized and then used in a CT algebraic reconstruction technique. This is a multispectral CT reconstruction, and the reconstructed data images are then detected, segmented and classified. This is accomplished by the fact that the density of a reconstructed object is determined by the attenuation which it causes in the scanning X-rays while the atomic number of the object is determined from the multiple energy scan output. In a classifier, the density and atomic number are compared to a stored look up table containing density and atomic number identification values for specific objects to be located.

After segmentation and classification, the data is sent to a computer coupled to a monitor where three dimensional CT scan data is displayed.

DESCRIPTION OF THE PREFERRED EMBODIMENT

Referring now to FIGS. 1–6, the basic continuous high speed tomographic imaging system indicated generally at 10 includes two conveyors 12 and 14 which are spaced to create a gap 16 between the conveyors. The conveyors operate to move a package 18 which contains a hidden object to be detected across the gap in the direction of the arrow in FIG. 2 at a speed sensed by a shaft encoder 19. Positioned in alignment with the gap 16 is a detector array 20 which receives a series of coplanar fan beams of X-ray photons directed vertically downwardly along a vertical scan plan designated by broken lines at 22 from an array of X-ray sources 24.

Figure 1:
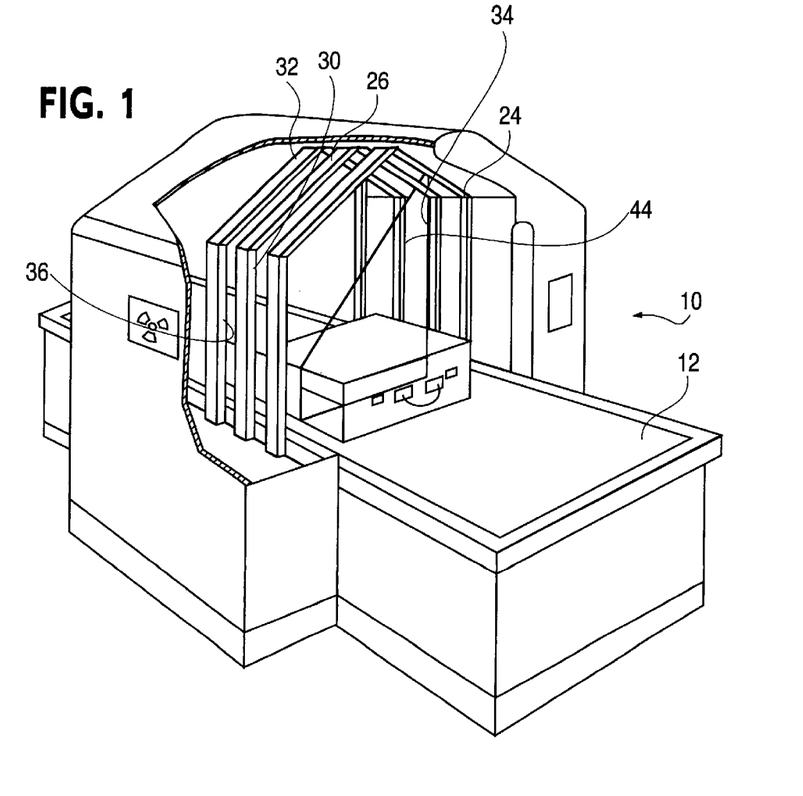
FIG. 1 is a perspective view of the continuous high speed tomographic imaging system of the present invention.
Figure 2:
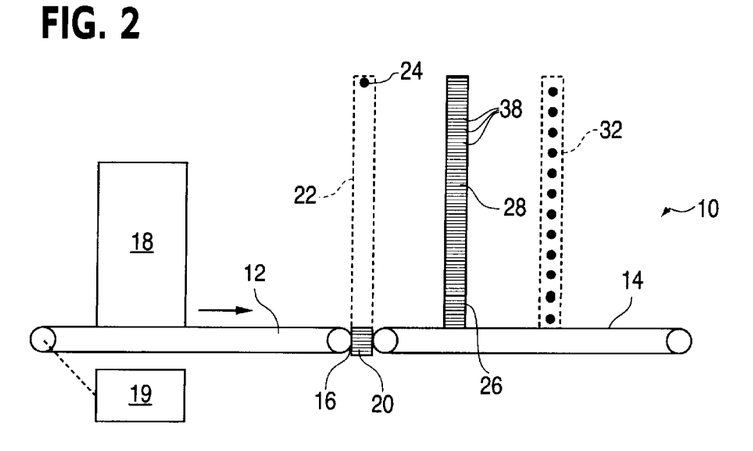
FIG. 2 is a diagrammatic view of the system of FIG. 1.

Spaced from the vertical scan plane 22 in the direction of travel of the package 18 is a horizontal left-right scan plane 26 along which a detector array 28 is positioned. The detector array 28 is positioned on the right side of the conveyor 14 while an array of X-ray sources 30 is positioned on the left side of this conveyor to direct X-ray photons across the conveyor to the detector array.

Finally, a horizontal right-left scan plane designated by the broken lines at 32 is spaced from the horizontal left-right scan plane 26 along the travel path of the package 18. Arranged on the right side of the conveyor 14 in alignment with the scan plane 32 is an array of X-ray sources 34 which transmit X-ray photons in the scan plane to a detector array 36 positioned on the left side of the conveyor 14 in alignment with the scan plane. Thus as the package 18 moves continuously along the conveyors 12 and 14, it is scanned a number of times as it moves through the scan planes 22, 26, and 32.

Each of the detector arrays 20, 28 and 36 is formed of a plurality of individual detector units 38 which are arranged in a line that is aligned with the fan shaped beams from the opposed X-ray sources. These detectors are mounted at evenly spaced intervals along each detector array to absorb photons from an X-ray source array and provide output pulses with peak voltage proportional to the energy of the photons.

Figure 6:
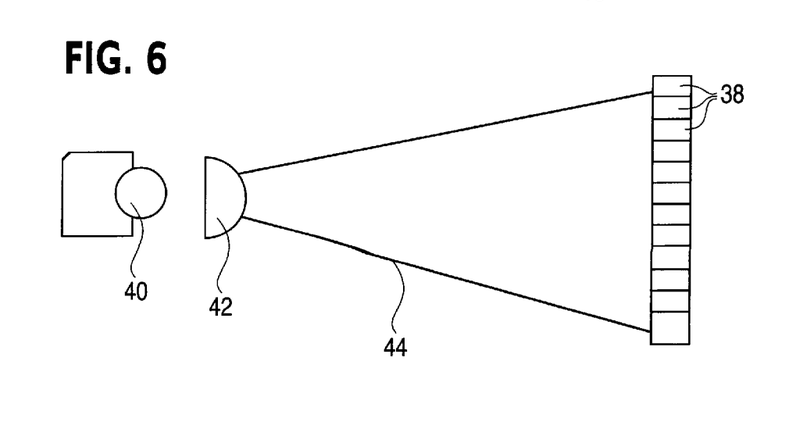
FIG. 6 is a diagrammatic view of an X-ray source and detector system of FIG. 1.

The X-ray source arrays 24, 30 and 34 each include a plurality of equally spaced individual X-ray photon sources 40, one of which is shown in FIG. 6. Each of the photon sources is collimated at 42 to provide a fan beam 44 of a desired beam thickness. Ideally, the fan beam will be collimated to a beam thickness in the order of 1 mm. over a distance of at least 141 cm. That is a divergence of 0.7 milliradians or 0.04°. Wider beam thickness results in an increase in the scatter background and the radiation leakage. To avoid such narrow collimation of the beam, it is possible to employ detector units 38 which are wider in the direction of package motion.

As the conveyors 12 and 14 move the package 18 through the scan planes 22, 26 and 32, a number of lines of projection image data are formed for the scanned package in each scan plane. These lines of projection image data show the attenuation of the X-rays by the package and its contents. The density of an object scanned within the package can be calculated from the attenuation of the X-rays caused by the object.

Figure 3:
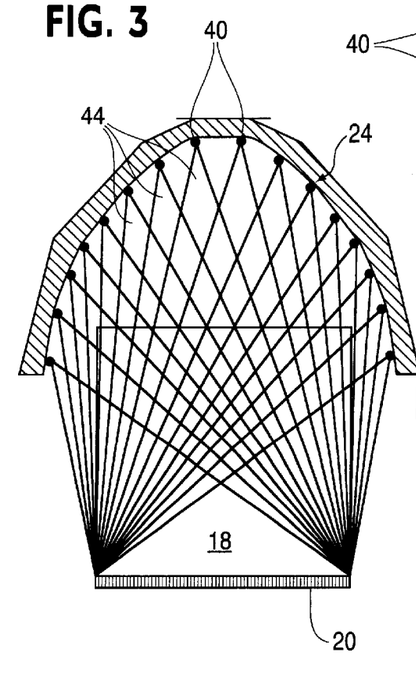
FIG. 3 is a diagrammatic view of a vertical scan plane X-ray source and detector system of FIG. 1.
Figure 4:
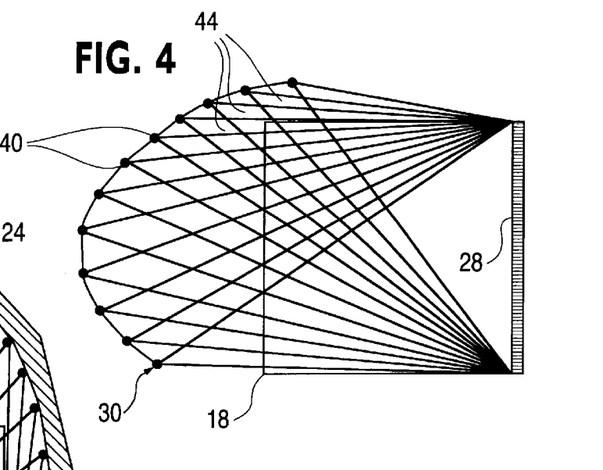
FIG. 4 is a diagrammatic view of a horizontal left-right scan plane X-ray source and detector system of FIG. 1.
Figure 5:
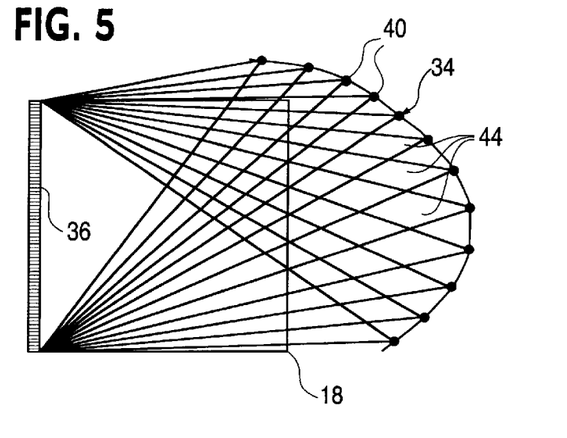
FIG. 5 is a diagrammatic view of a horizontal right-left scan plane X-ray source and detector system of FIG. 1.

When multiple X-ray sources 40 producing fan beams are arranged in a straight line, sources located near the center of a side of the image area will provide a higher intensity beam on a detector array aligned in a straight line since intensity decreases with the square of d, the distance of the source from the detector element. Since the output of the detector elements of the detector array for all source locations should be equal, in the absence of a package 18, it becomes necessary to progressively reduce the current for source locations as they approach the center of a side of the image for straight line source arrays. The same effect of maximizing the dynamic range of the system by substantially equalizing the output of the detectors in the detector array can also be achieved by curving the source array as shown in FIGS. 3–5 to progressively increase the distance between the sources and the detector arrays as the sources approach the center of the image area. This configuration provides substantially better coverage of the image area.

FIG. 3 illustrates an arrangement of source 40 locations for the top-down scan plane 22. Sixteen source locations are indicated producing equal detector outputs in the absence of the package 18 assuming that the output is proportional to $\cos(a)\delta 2$ where $\delta$ is the angle between the source-detector ray and perpendicular to the detector. The source locations at the sides can be about 7 inches, or 17 cm., from the image area. All points in the lower triangle are crossed by sixteen paths. Moving out of that triangle, the number of ray paths decreases by one as one crosses any of the lines, and almost all points are crossed by at least four paths. The maximum $\delta$ is less than 55°.

FIG. 4 illustrates the source array geometry for the left-right scan plane 26 and FIG. 5 illustrates the source array geometry for the right left scan plane 32, which is the mirror image of the source geometry of FIG. 4. The source geometries of FIGS. 4 and 5 are essentially the same as that of FIG. 3 with the exception that four source locations that would create ray paths through the belt of the conveyor 14 have been eliminated, leaving twelve source locations which scan above the upper surface of the belt 14. The scan planes of FIGS. 4 and 5 contribute mostly to resolution along the right and left sides of the image respectively. However, they also contribute substantially over the whole image.

By using the three scan planes 22, 26 and 32, almost every point in the image area is crossed by at least 14 ray paths. The bottom of the image area is covered by at least 18 ray paths, the center is crossed by 32 ray paths and the top center is crossed by 12 ray paths. Most points are crossed by ray paths over a range of 180°, although the distribution of path angles is irregular through many points.

To adapt the system for multispectral CT reconstruction, each detector array 20, 28 and 36 outputs five energy levels for each scan to provide multiple energies for the same set of data points. Systems of this type which use multiple filters to obtain multi-energy outputs from a detector are known. Alternatively, the detector systems can be constructed so that each detector provides an output signal to five comparators, each of which receives a different threshold voltage from a threshold source. The output of each comparator is a different energy level signal which represents the intensity of the spectral range above the comparator threshold input. The proportional decrease in the number of photons is a function of material chemical composition (i.e. atomic number).

Figure 7:
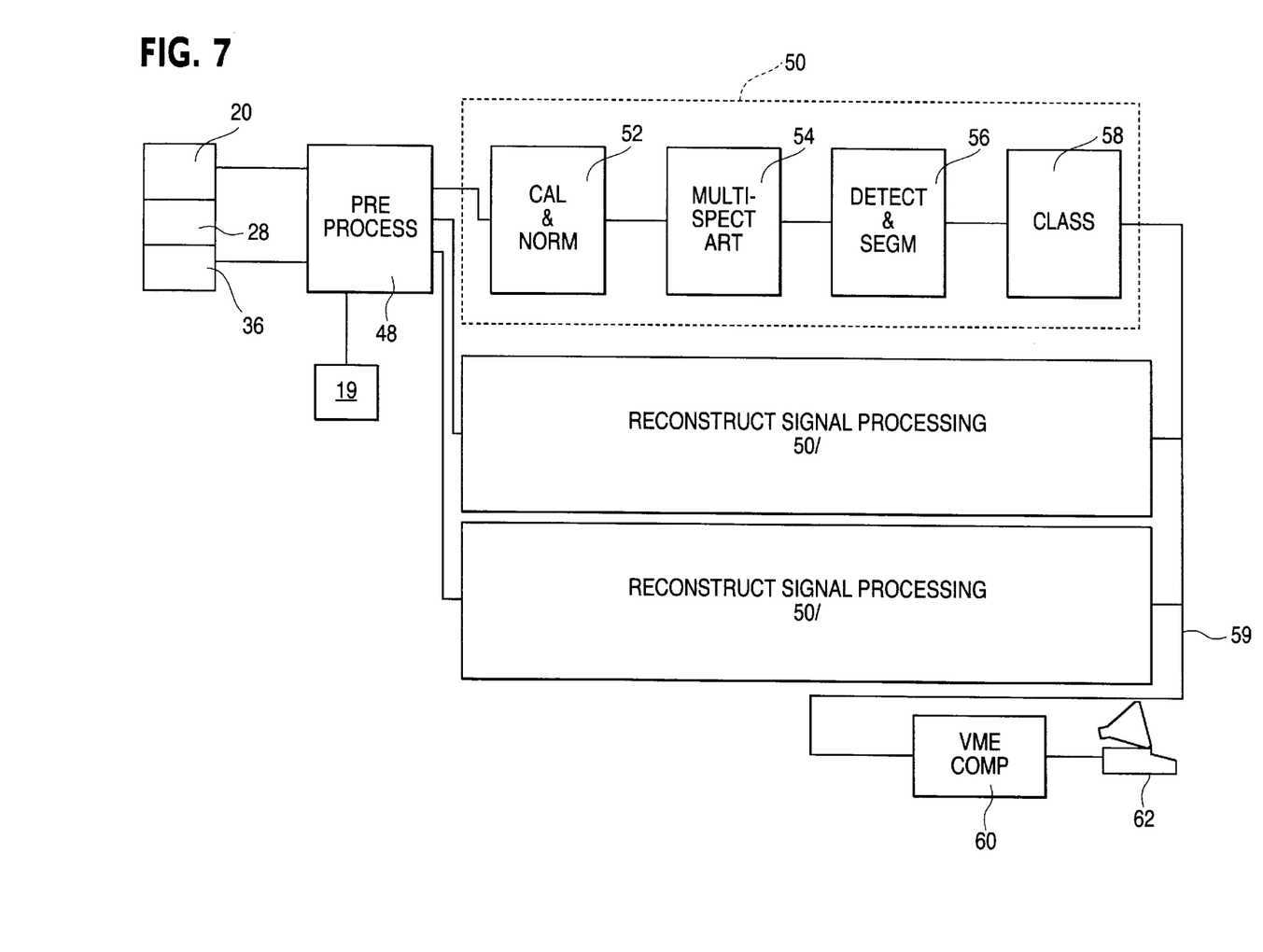
FIG. 7 is a block diagram of the processing and analysis assembly for the continuous high speed tomographic imaging system of the present invention.

The processing and analysis assembly for the tomographic imaging system 10 is illustrated in FIG. 7. The assembly receives inputs from a sensor unit 46 which includes the detector arrays 20, 28 and 36. A preprocessing unit 48 interfaces directly with the sensor units to provide buffering of the output data received from the sensor units. Timing is controlled by an input from the shaft encoder 19. Once the five level input has been received and stored by the preprocessing unit from each of the detector arrays for a single scan, an address generator in the preprocessing unit which is connected to a plurality of reconstruction signal processing boards 50 generates a board address to determine which of the reconstruction signal processing boards will receive a current frame of data.

Each reconstruction board contains up to 16 computer chips, and the systems for the boards are shown in detail for one board in FIG. 7. These systems cooperate to provide calibration and normalization of the raw input data at 52, and then conventional multispectral CT reconstruction at 54 which includes algebraic reconstruction in accordance with the novel technique to be described. During reconstruction, each slice through the package 18 is reconstructed at five different energies which are required to obtain the atomic number of a sensed object.

The algebraic reconstruction data from 54 is sent to a detection and segmentation section 56 which detects the atomic number and density of a scanned object. For most materials, the linear X-ray attenuation coefficient mu is proportioned to the density. Thus the logarithm of the relative intensity of the X-ray beam is proportioned to the integral of the density of the material within the beam.

The density and atomic number information is compared in a classification unit 58 with a stored look-up table containing density and atomic number information for specific objects to be identified. This identification data and the reconstructed image data is then sent over a VME bus 59 to a VME computer 60 for an operator console 62. The reconstructed CT image data is displayed on the operator console.

We have examined potential algorithms for reconstruction of images from arbitrary sensor and source geometries. There are two classes of possible methods: algebraic reconstruction techniques, (ART), and direct inversion. Both methods solve the discrete matrix equation, $$W\vec{F}=\vec{P}. \quad (1)$$

where $\vec{F}$ is a vector of attenuation coefficients, which form the image, $\vec{P}$ is the vector of observed log attenuations, and W is a matrix of weights, determined by the geometry. $W_{ij}$ is the weight that picture element j has in affecting attenuation along projection i.

Direct inversion would provide an exact least squares solution of equation 1. That is, the computed image matrix would provide projections which deviate as little as possible in the mean squares sense from the observed attenuations. This does not guarantee that the image would be satisfactory, however. The inversion may be unstable: unacceptably sensitive to noise and to imperfections in geometry. Possible approaches to direct inversion include singular value decomposition of W or inversion of the symmetric matrix $W^T W$ to provide the solution $$\vec{F}=(T^W T)^{-1}W^T\vec{P}. \quad (2)$$

Either approach is challenging because of the size of W. For example, if there are 10,000 pixels and 32,000 projections then W has 320×10$^6$ elements, and it is symmetric, so only half the elements have to be stored. Either approach to inversion would provide valuable quantitative information about the stability of the inversion. Our initial evaluation is that the advantages of symmetry probably would be easier to exploit than the sparseness of W. However, with suitable implementation, the ART approach has proved so successful that further investigation of direct inversion is probably not warranted.

ART algorithms create a reconstructed image with a plurality of spaced pixels. All ART algorithms are based on successive approximate solution of equation 1, row by row, that is, projection by projection. That is, from an arbitrary starting image, $\vec{F}(0)$, successive images are defined to provide the observed attenuations along successive projections:

$$W\vec{F}(k)=\vec{P}(k). \quad (3)$$

The successive approximations are derived by the method of steepest descent. That is, $\vec{F}$ is changed as little as possible to satisfy each successive projection. Because this is an entirely linear problem, the method can be proven to converge, after an indefinite number of cycles through all the projections, if equation 1 has an exact solution. If there is no exact solution, (due to noise), the least squares solution can be found by limiting the change in each successive approximation to a fraction of the change required for an exact solution.

Although this might seem to be a complete definition of the ART algorithm, there are, in fact, at least as many variations as there are investigators. After review of the literature and evaluation of the MIPG software package from the University of Pennsylvania containing leading variations, we concluded that none of them work satisfactorily. The proliferation of variants probably exists because previous investigators have made the same observation. All of the methods suffer from severe streaking. That is, strong contrasts in attenuation cause perturbations which extend over a significant fraction of the image. The shapes and locations of these streaks vary with the method and with the geometry of sources and detectors, but, except in the most ideal geometries, our qualitative evaluation is that the absorption spectra in individual pixels would be too distorted to provide reliable discrimination of materials.

On the other hand, given the fact that successive approximation provides an exact solution of equation 1, we believe that all the existing methods employ unstable formulations of that equation. Most importantly, they compute the weight matrix, W, using inappropriate and unstable representations of the digital image. We believe that our formulation is significantly more stable and that the results demonstrate a significant improvement, adequate for spectroscopic discrimination of materials with a practical geometry. Real time implementation is definitely feasible.

The primary cause of the instability in most formulations of equation 1 is naive interpretation of the meaning of a digital image. Typically, the grid of pixel values is interpreted to represent a grid of disjoint, sharp-edged tiles, each containing a uniform attenuation coefficient. A digital image, with one pixel value per tile, is not an adequate representation of such a structure, unless the actual attenuation in the object to be imaged has exactly that same tile structure, which it certainly will not. As Nyquist demonstrated, and as is common knowledge in signal processing, a sampling can consistently represent a continuous signal or image only if the shortest wavelength in that image is greater than twice the sampling interval. A familiar example is the attempt to represent a square wave or step function signal, which contains arbitrarily high frequency components, with a finite bandwidth Fourier approximation. Ringing is inevitably produced around the steps in the signal. The image inversion problem is more complex, but related. Streaks are almost inevitably generated if weight functions for projections change by significant amounts between ray paths separated by a small distance compared to the interval between pixels.

Appropriate, stable inversion of the projection data requires two steps which are not typically included in ART reconstruction. First, attenuations from adjacent projections should be low pass filtered to remove variations with wavelengths shorter than twice the pixel interval. Detectors which average the signal over distances comparable to the distance between pixels provide some filtering. With a very high detector density, much more effective filtering can be applied.

Second, the reconstruction should be in terms of basis functions which contain little variation over intervals of the pixel spacing. That is, the attenuation in the image area must be modeled as the sum of smooth functions with diameters of at least two pixel intervals. The inversion defines amplitudes for the basis functions which best fit the measured projection attenuations. The value appropriate for an image pixel is then the sum of the basis functions, times their amplitudes, at the pixel position.

Figure 8:
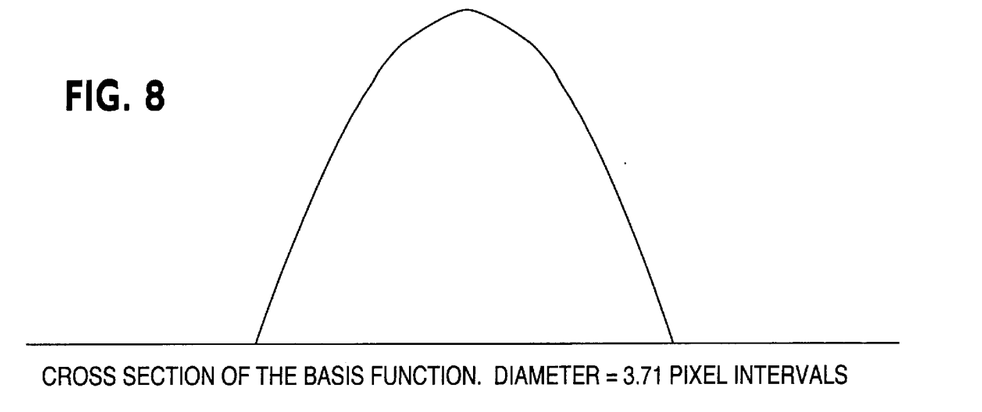
FIG. 8 is a cross section diagram of a basis function used for the basis function ART of the present invention.

In the current algorithm, we employ a square grid of basis functions, centered at the pixel locations, all of the same form and diameter, although none of these restrictions is necessary. The basis functions have the form $$f(r) = \frac{3}{4}(R^2 - r^2), \ r < R; \ F = 0, \ r > R,$$

where r is the distance from the center and distances are in units of the pixel spacing. $R^2 = 3.45$ provides the smoothest sum of basis function for any value of R between 1 and 2. FIG. 8 illustrates the shape of this basis function. This form was chosen primarily for analytic convenience. Any comparably smooth function should provide comparable performance.

Figure 9:
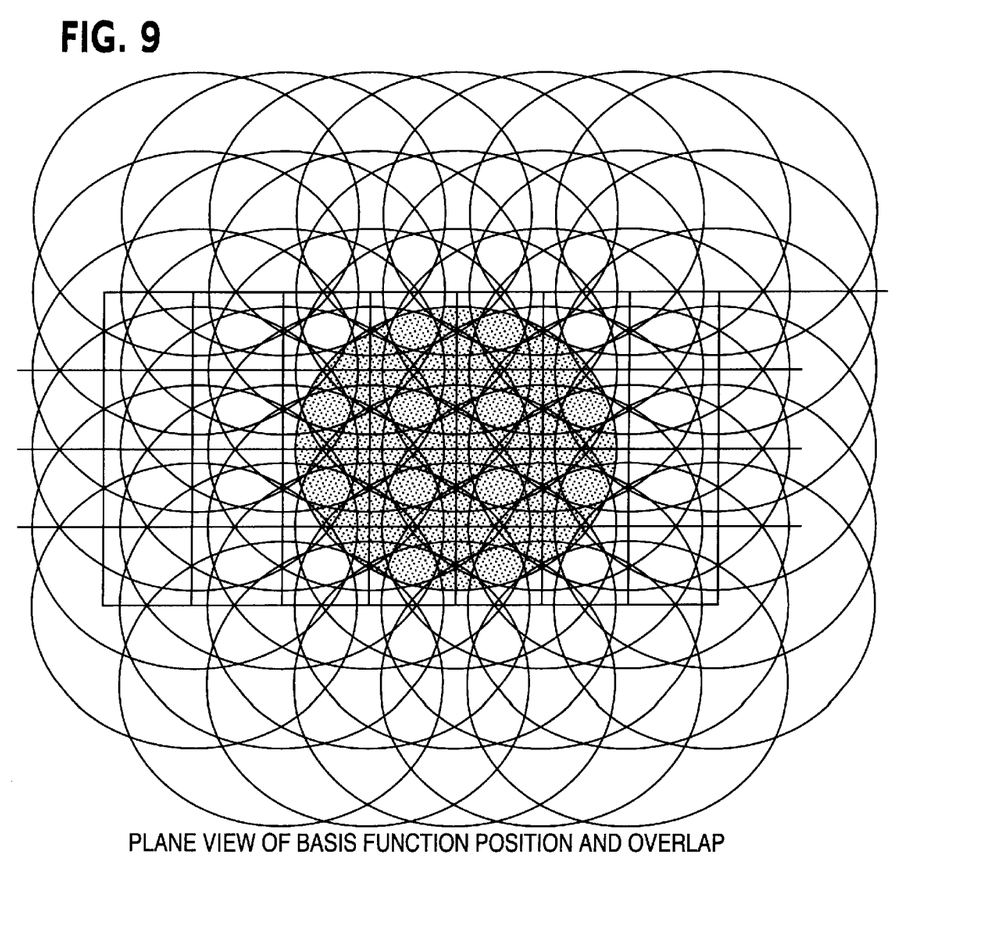
FIG. 9 is a diagrammatic plane view showing the basis function position and overlap for the basis function ART of the present invention.

FIG. 9 is a plan view of basis functions with this radius and their overlap. One basis function is filled to make it distinct. The pixel positions and the centers of the basis functions are indicated by the intersections of the straight lines. Note that each basis function overlaps nine adjacent pixel locations.

Figure 10:
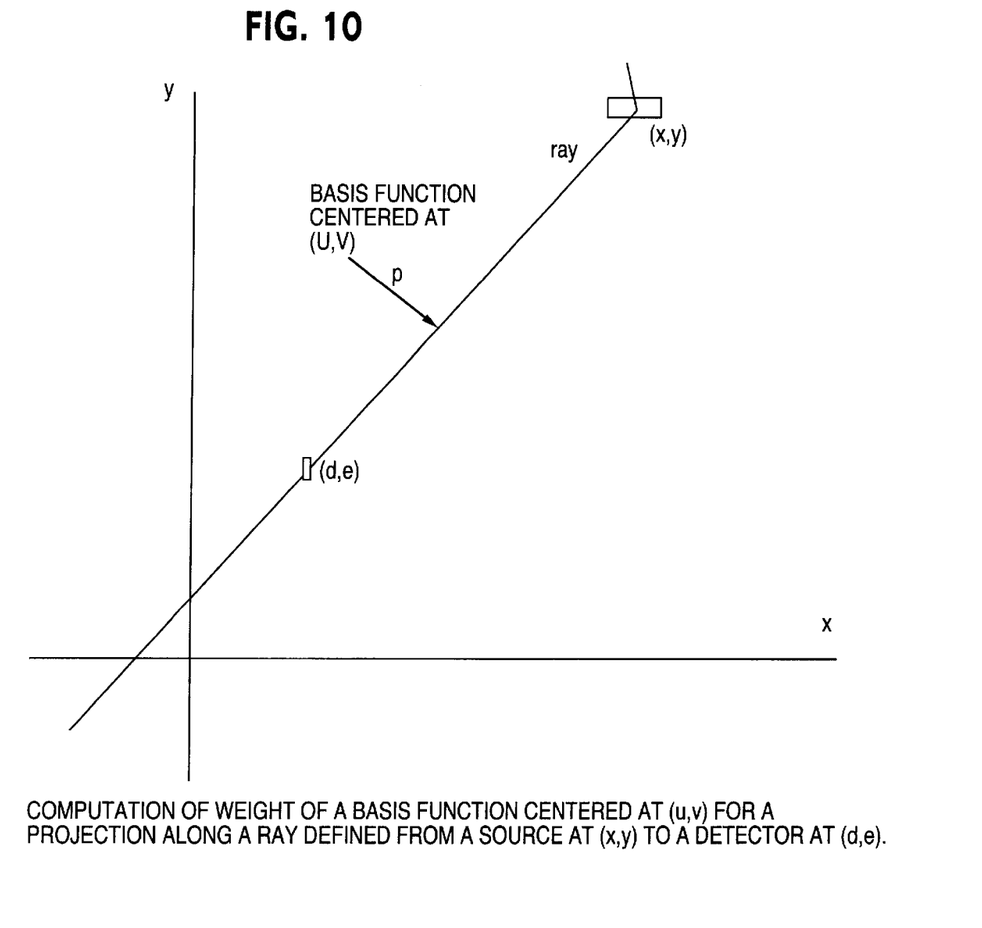
FIG. 10 is a diagrammatic view of the computation of weight of a basis function for a projection along a ray path in accordance with the basis function ART of the present invention.

The weight for a basis function, for a projection along a given ray, is equal to the line integral of the ray over the function. This is equal to $$2 \int_{|p|}^{R} f(\eta) \frac{\eta}{\sqrt{\eta^2 - |p|^2}} d\eta = \quad (4)$$

$$\frac{3}{2} \int_{|p|}^{R} \left[ R^2 \sqrt{\eta^2 - |p|^2} - \frac{1}{3}\sqrt{(\eta^2 - |p|^2)^3} - |p|^2 \sqrt{\eta^2 - |p|^2} \right] =$$

$$(R^2 - |p|^2)^{\frac{3}{2}},$$

where [p] is the closest approach of the ray to the basis function center, illustrated in FIG. 10.

$$|p|^2 = (d-u)^2 + (e-v)^2 - \frac{((d-u)(d-x) + (e-v)(e-y))^2}{(d-x)^2 + (e-y)^2} \quad (5)$$

FIG. 9 demonstrates that the overlap of the basis functions is rather complex. However, the total weight of a ray path in crossing any given row can be computed rather easily. This weight is ideally independent of the position at which the ray crosses the row. The maximum weight in a row for a ray crossing that row perpendicularly is 14.0777, crossing a grid point or half way between, and the minimum is 13.965. The variation is less if the ray crosses at any other angle.

Once the projection measurements have been inverted to provide the amplitudes of the basis functions, the pixel values are computed by a convolution. As illustrated in FIG. 9, since each basis function overlaps nine adjacent pixels, the convolution kernel is 3×3 with the values of the basis function at these points. This kernel is:

| 348 | 588 | 348 |
| 588 | 828 | 588 |
| 348 | 588 | 348 |

This convolution greatly increases the stability of the individual pixel values and thus provides the best estimate of the image in the sense of minimizing the deviation of the inversion from the original. However, the basis function amplitudes can also be presented as an image. This basis function image is "sharpened", similar to the image that would be produced by convolving the image with a differential kernel to accentuate edges and other short wavelength structure.

We claim:

1. A continuous, high speed, tomographic imaging apparatus for detecting target objects contained within a moving package comprising:

a package conveying system for continuously conveying a package along a line of travel between a conveying system input end and a conveying system output end, first, second and third spaced CT scanning stations relatively spaced along said line of travel and positioned between the conveying system input and output ends for scanning said moving package in three different scan planes relatively spaced along said line of travel, each said CT scanning station including a plurality of spaced, stationary X-ray sources all positioned to project X-ray beams in the same scan plane and a stationary detector array positioned in opposed, spaced relationship to said X-ray sources, said detector array including a plurality of stationary, spaced detectors to receive X-ray beams projected from said X-ray sources in said scan plane and to provide CT data output signals which are a function of the received X-ray beams, said first CT scanning station operating in a scan plane which is vertically oriented relative to said line of travel, said second and third CT scanning stations each operating in a scan plane which is transverse to said line of travel, the X-ray sources of said second CT scanning station projecting beams from the right side of said line of travel to the left side thereof and the X-ray sources of said third CT scanning station projecting beams from the left side of said line of travel to the right side thereof, and a processing and analysis assembly connected to receive said detector CT output signals from the detector arrays of said first, second and third CT scanning stations, said processing and analysis assembly operating to analyze said CT data output signals to identify target objects.

2. The continuous, high speed, tomographic imaging apparatus of claim 1 wherein each of said CT scanning stations operates to scan the same cross sectional slice of said package, said processing and analysis section including storage means to store CT data output signals from said CT scanning stations until CT output signals from all three CT scanning stations derived from scanning the same cross-sectional slice of said package have been received by said processing and analysis section.

3. The continuous, high speed, tomographic imaging apparatus of claim 2 wherein said package conveying system includes a conveyor having first and second conveying sections separated by a gap, said first and second conveying sections having co-planar upper conveying surfaces, the X-ray sources of said first CT scanning station projecting X-ray beams in said gap past said upper conveying surfaces.

4. The continuous high speed tomographic imaging apparatus of claim 3 wherein the X-ray sources of said second and third CT scanning stations project X-ray beams above and across said upper conveying surfaces.

5. The continuous, high speed, tomographic imaging system of claim 4 wherein said second and third CT scanning stations include an equal number of X-ray sources, said first CT scanning station including a greater number of X-ray sources than the number of X-ray sources in said second and third CT scanning stations.

6. The continuous, high speed, tomographic imaging apparatus of claim 2 wherein the stationary X-ray sources of said first, second and third CT scanning stations project X-ray beams which result in CT data output signals of equal intensity from each of the detectors for the respective CT scanning station in the absence of a package passing by said scanning station.

7. The continuous, high speed, tomographic imaging apparatus of claim 6 wherein the stationary detector array for each first, second and third CT scanning station includes a plurality of detectors arranged in a straight line, said plurality of X-ray sources for each CT scanning station being arranged in a curved configuration to progressively increase the distance between the X-ray sources and the detector array as the X-ray sources approach the center of an image area detected by the detector array, the distances between the X-ray sources for each CT scanning station and the detectors in the stationary detector array being such that CT data output signals of equal intensity are provided by each of the detectors for a CT scanning station in the absence of a package passing by said scanning station.

8. The continuous, high speed, tomographic imaging apparatus of claim 2 wherein each of said stationary X-ray sources for a CT scanning station projects an X-ray fan beam coplanar with the fan beams projected by other X-ray sources in the same scanning station.

9. The continuous, high speed, tomographic imaging apparatus of claim 8 wherein each X-ray source provides a fan beam having a thickness of 1 mm over a distance of at least 141 cm.

10. The continuous, high speed, tomographic imaging apparatus of claim 8 wherein each of said detectors of the detector arrays for said first, second and third CT scanning stations provide CT output signals from the same scan having five different energy levels, said processing and analysis assembly receiving and processing the five energy levels from a scan to achieve a multispectral reconstruction to determine a chemical characteristic of a target object scanned.

11. The continuous, high speed, tomographic imaging apparatus of claim 10 wherein said processing and analysis assembly receives and processes the CT output signals from said detector arrays to determine the density of a target object.

12. The continuous, high speed, tomographic imaging apparatus of claim 11 wherein said processing and analysis assembly includes a classification unit for receiving said chemical characteristic and density determined for a target object and comparing said density and chemical characteristic to a lookup table of densities and chemical characteristics for a known group of target objects to identify the scanned target object.

13. The continuous, high speed, tomographic imaging apparatus of claim 12 wherein said processing and analysis section including a CT ART reconstruction section for receiving the stored CT data output signals from said three CT scanning stations for the same cross-sectional slice of said package and for reconstructuring from such CT data output signals a tomographic image of the scanned cross-sectional slice of said package.

14. The continuous, high speed, tomographic imaging apparatus of claim 13 wherein the stationary detector array for each first, second and third CT scanning station includes a plurality of detectors arranged in a straight line, said plurality of X-ray sources for each CT scanning station being arranged in a curved configuration to progressively increase the distance between the X-ray sources and the detector array as the X-ray sources approach the center of an image area detected by the detector array.

15. The contiguous, high speed, tomographic imaging system of claim 14 wherein each X-ray source provides a fan beam having a thickness of 1 mm over a distance of at least 141 cm.

16. A method for detecting a target object within a continuously moving container comprising the steps of:
CT scanning the container with a plurality of adjacent X-ray projections to obtain a plurality of CT output signals attenuated by the scanned container, using an ART to create a reconstructed image having a plurality of spaced pixels with a defined pixel interval from said CT output signals including
low pass filtering attenuated CT output signals from adjacent X-ray projections to remove variations with wavelengths shorter than twice the pixel interval and
reconstructuring said image by modeling attenuation in the image area as the sum of smooth basis functions with diameters of at least two pixel intervals.

17. The method of claim 16 wherein said basis functions are formed to overlap.

18. The method of claim 17 wherein each basis function overlaps nine adjacent pixel locations.

* * * * *